(12) United States Patent
Tang et al.

(10) Patent No.: US 11,045,094 B2
(45) Date of Patent: *Jun. 29, 2021

(54) PATCH-BASED PHYSIOLOGICAL SENSOR

(71) Applicant: TOSENSE, INC., San Diego, CA (US)

(72) Inventors: Erik Tang, San Diego, CA (US);
Matthew Banet, San Diego, CA (US);
Marshal Dhillon, San Diego, CA (US);
James McCanna, Pleasanton, CA (US)

(73) Assignees: BAXTER INTERNATIONAL INC., Deerfield, IL (US); BAXTER HEALTHCARE SA, Glattpark (CH)

(*) Notice: Subject to any disclaimer, the term of this patent is extended or adjusted under 35 U.S.C. 154(b) by 4 days.

This patent is subject to a terminal disclaimer.

(21) Appl. No.: 16/044,411

(22) Filed: Jul. 24, 2018

(65) Prior Publication Data

US 2020/0029826 A1 Jan. 30, 2020

(51) Int. Cl.
| | |
|---|---|
| *A61B 5/0205* | (2006.01) |
| *A61B 5/00* | (2006.01) |
| *A61B 5/0428* | (2006.01) |
| *A61B 5/0404* | (2006.01) |
| *G05D 23/19* | (2006.01) |
| *A61B 5/30* | (2021.01) |

(Continued)

(52) U.S. Cl.
CPC ............ *A61B 5/0205* (2013.01); *A61B 5/303* (2021.01); *A61B 5/332* (2021.01); *A61B 5/6822* (2013.01); *A61B 5/6823* (2013.01); *G05D 23/19* (2013.01); *A61B 5/02433* (2013.01); *A61B 5/02438* (2013.01); *A61B 2560/0266* (2013.01); *A61B 2562/0271* (2013.01); *A61B 2562/063* (2013.01); *A61B 2562/164* (2013.01)

(58) Field of Classification Search
CPC .............. A61B 5/02438; A61B 5/6822; A61B 2562/0271
See application file for complete search history.

(56) References Cited

U.S. PATENT DOCUMENTS

| 8,364,250 B2 | 1/2013 | Moon et al. |
| 8,449,469 B2 | 5/2013 | Banet et al. |

(Continued)

OTHER PUBLICATIONS

Mendelson and Ochs, Noninvasive Pulse Oximetry Utilizing Skin Reflectance Pho toplethy smog mphy. IEEE Trans Biomed Eng. Oct. 1988;35(10):798-805.

(Continued)

*Primary Examiner* — Gary Jackson
*Assistant Examiner* — Zahed Kabir
(74) *Attorney, Agent, or Firm* — K&L Gates LLP

(57) ABSTRACT

The invention provides a neck-worn sensor for simultaneously measuring a blood pressure (BP), pulse oximetry (SpO2), and other vital signs and hemodynamic parameters from a patient. The neck-worn sensor features a sensing portion having a flexible housing that is worn entirely on the patient's chest and encloses a battery, wireless transmitter, and all the sensor's sensing and electronic components. It measures electrocardiogram (ECG), impedance plethysmogram (IPG), photoplethysmogram (PPG), and phonocardiogram (PCG) waveforms, and collectively processes these to determine the vital signs and hemodynamic parameters. The sensor that measures PPG waveforms also includes a heating element to increase perfusion of tissue on the chest.

30 Claims, 11 Drawing Sheets

(51) Int. Cl.
*A61B 5/332* (2021.01)
*A61B 5/024* (2006.01)

(56) References Cited

U.S. PATENT DOCUMENTS

| | | | |
|---|---|---|---|
| 8,475,368 B2 | 7/2013 | Tran et al. | |
| 8,506,480 B2 | 8/2013 | Banet et al. | |
| 8,527,038 B2 | 9/2013 | Moon et al. | |
| 8,727,977 B2 | 5/2014 | Banet et al. | |
| 8,740,807 B2 | 6/2014 | Banet et al. | |
| 9,149,577 B2 | 10/2015 | Robertson et al. | |
| 9,215,986 B2 | 12/2015 | Banet et al. | |
| 9,339,209 B2 | 5/2016 | Banet et al. | |
| 9,380,952 B2 | 7/2016 | Banet et al. | |
| 9,597,004 B2 | 3/2017 | Hughes et al. | |
| 9,700,222 B2 | 7/2017 | Quinlan et al. | |
| 9,735,893 B1* | 8/2017 | Aleksov | A61B 5/14546 |
| 9,901,274 B2 | 2/2018 | Bishay et al. | |
| 2008/0114220 A1* | 5/2008 | Banet | A61B 5/6833 |
| | | | 600/301 |
| 2015/0119728 A1* | 4/2015 | Blackadar | G16H 20/30 |
| | | | 600/484 |
| 2016/0029964 A1* | 2/2016 | LeBoeuf | A61B 5/165 |
| | | | 600/476 |
| 2016/0106366 A1* | 4/2016 | Banet | A61B 5/6822 |
| | | | 600/301 |
| 2016/0198972 A1 | 7/2016 | Lee et al. | |
| 2016/0302674 A1* | 10/2016 | Moyer | A61B 5/0002 |
| 2016/0331257 A1 | 11/2016 | Baumann et al. | |
| 2017/0000359 A1* | 1/2017 | Kohli | A61B 5/02055 |
| 2017/0000371 A1 | 1/2017 | Quinlan et al. | |
| 2017/0000372 A1 | 1/2017 | Quinlan et al. | |
| 2017/0119305 A1 | 5/2017 | Bardy et al. | |
| 2017/0135595 A1 | 5/2017 | Baek et al. | |
| 2017/0143264 A1 | 5/2017 | Paquet et al. | |
| 2017/0164860 A1 | 6/2017 | Hung et al. | |
| 2017/0188871 A1 | 7/2017 | Bishay et al. | |
| 2017/0188872 A1 | 7/2017 | Hughes et al. | |
| 2017/0196761 A1* | 7/2017 | Hyde | A61H 9/0057 |
| 2017/0265770 A1 | 9/2017 | Quinlan et al. | |
| 2017/0347899 A1* | 12/2017 | Bhushan | A61B 5/02055 |
| 2020/0008299 A1* | 1/2020 | Tran | H05K 1/0393 |

OTHER PUBLICATIONS

Mendelson and McGinn, Skin reflectance pulse oximetry: in vivo measurements from the forearm and calf. J Clin Monit. Jan. 1991;7(1):7-12.

* cited by examiner

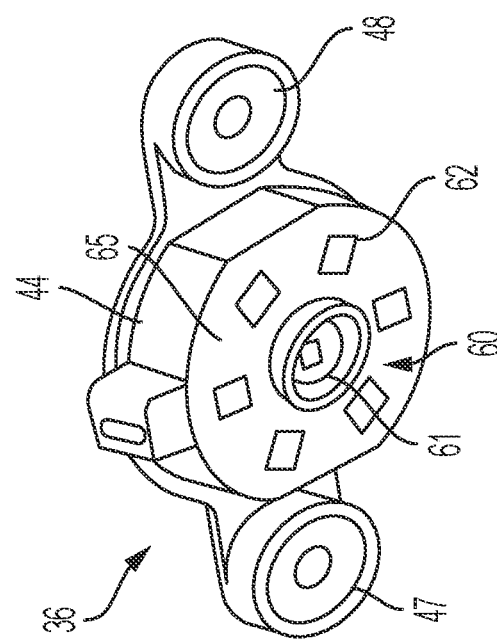
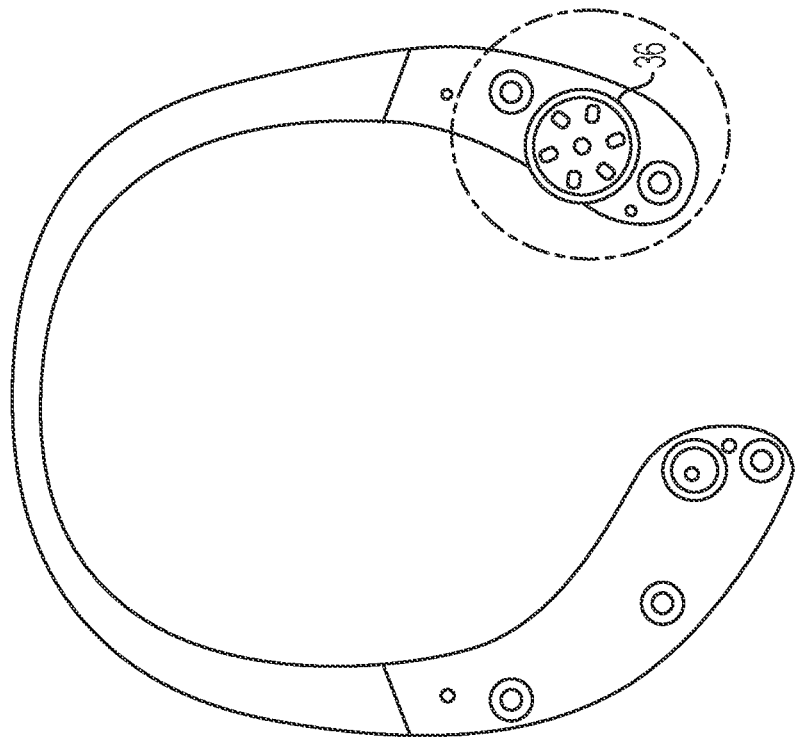
Fig. 3B
Fig. 3A

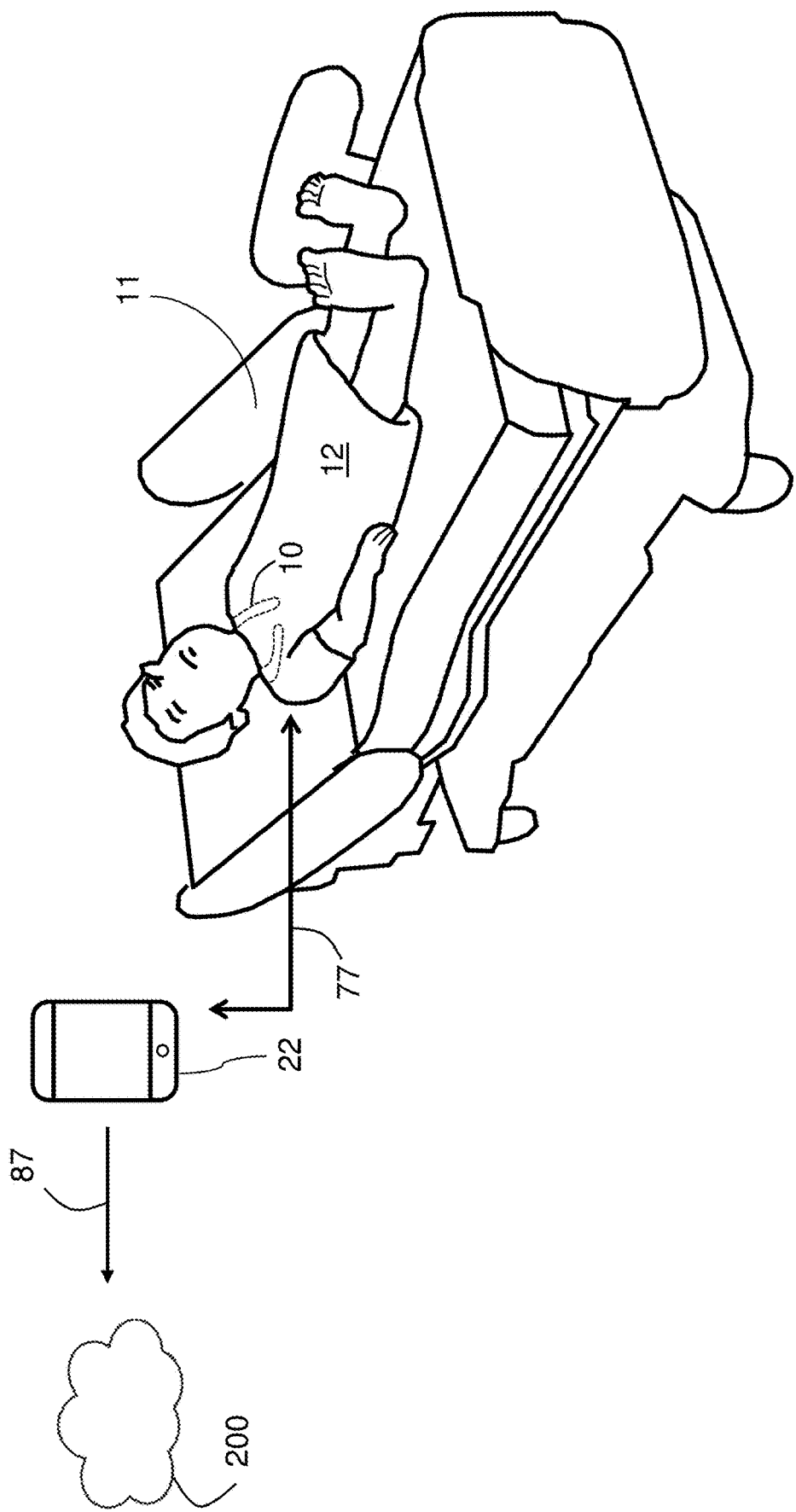

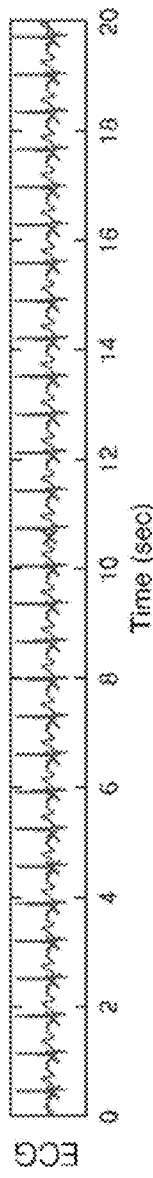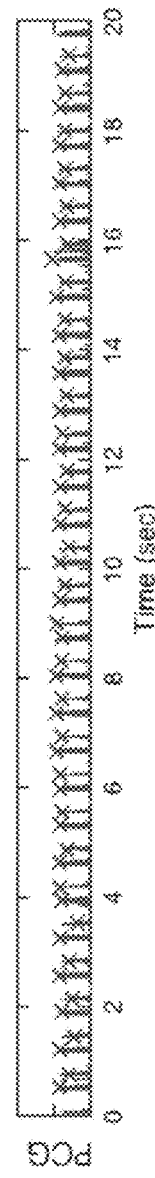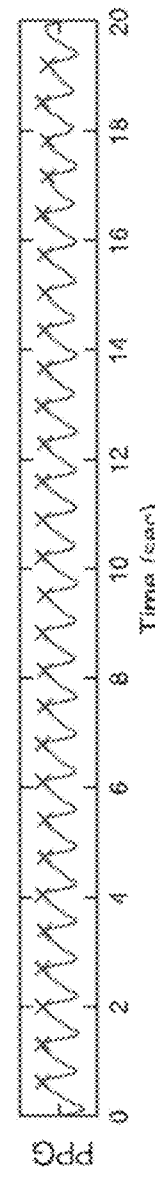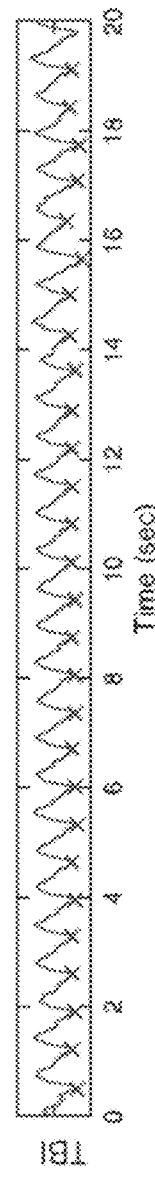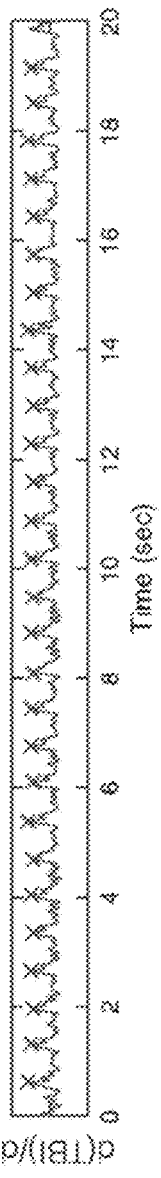

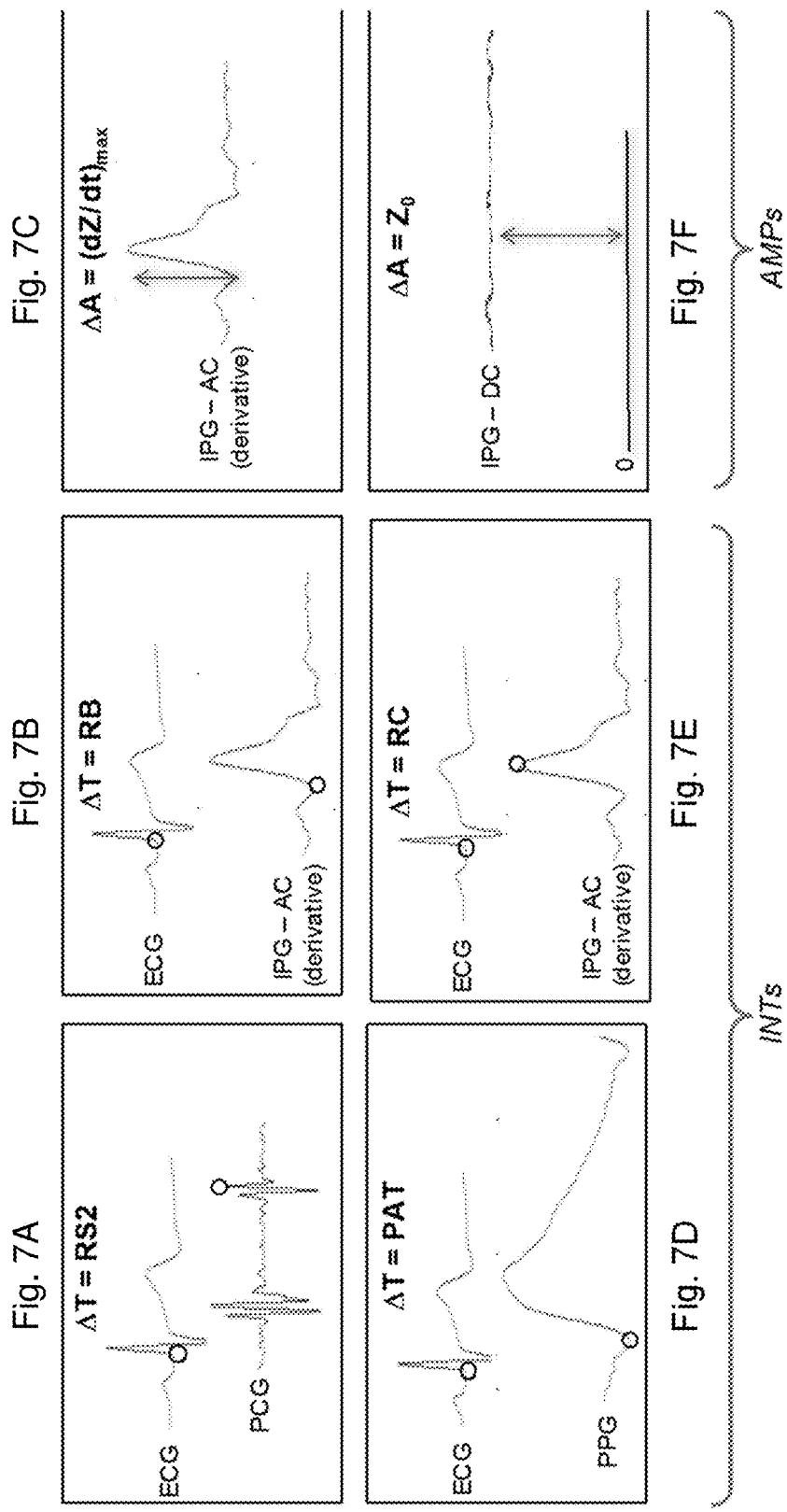

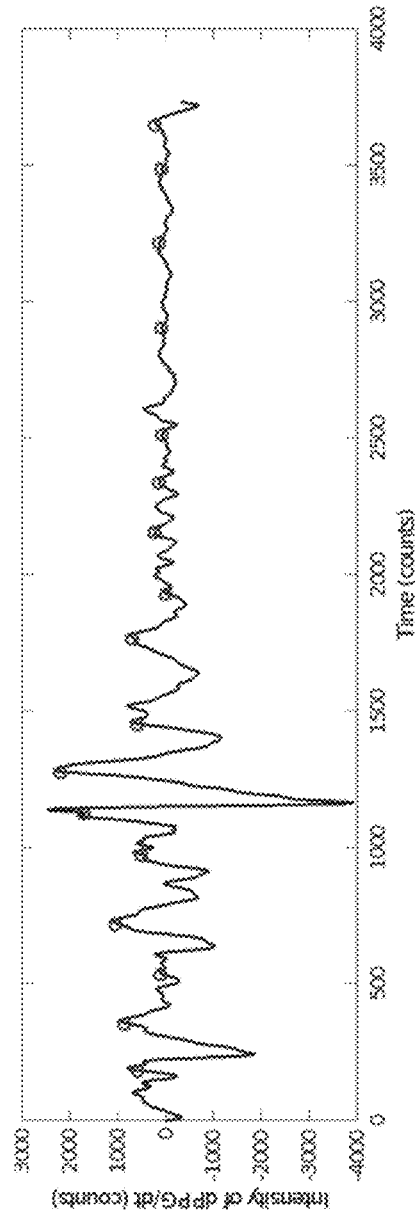
Fig. 8A Before Heat
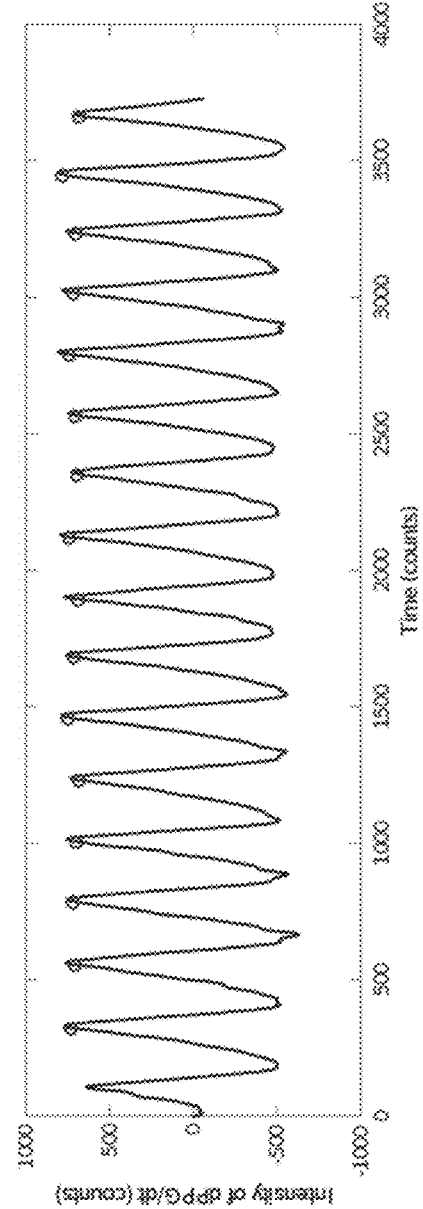
Fig. 8B After Heat

| Unit ID | Col2 | Col3 | Col4 | Col5 | Col6 | Col7 | Col8 | Col9 | Col10 |
|---|---|---|---|---|---|---|---|---|---|
| 3001 | 144 | 44 | 10.2 | 3.2 | RR S1S2 | 92 | 28 | 5.2 | 3.8 | RR RC |
| 3002 | 160 | 48 | 7.5 | -1.8 | RR RC | 112 | 42 | 7.5 | 3.9 | RC DZ |
| 3003 | 136 | 26 | 4.2 | -3.1 | RR DZ | 96 | 24 | 5.8 | 3.6 | RR SV |
| 3004 | 154 | 44 | 6.9 | 4.8 | RR RC | 94 | 34 | 8.7 | -11.0 | RR SV |
| 3005 | 156 | 48 | 10.0 | 9.8 | RR S1S2 | 94 | 30 | 7.3 | 9.5 | RR RC |
| 3006 | 134 | 42 | 7.7 | 7.8 | RR DZ | 100 | 40 | 7.3 | 2.2 | RR RC |
| 3010 | 140 | 32 | 4.6 | 0.7 | RR S1S2 | 108 | 38 | 3.7 | 4.7 | RR RC |
| 3011 | 146 | 36 | 3.8 | 1.5 | RR SV | 88 | 32 | 9.5 | -3.0 | RR DZ |
| 3012 | 134 | 36 | 7.7 | 2.2 | RR SV | 80 | 34 | 11.2 | -3.0 | S1S2 DZ |
| 3013 | 156 | 36 | 10.1 | 3.2 | RR RC | 108 | 28 | 7.5 | 1.2 | RR DZ |
| 3015 | 144 | 42 | 7.8 | 9.2 | RR S1S2 | 94 | 36 | 8.3 | 3.4 | RR DZ |
| 3016 | 168 | 30 | 9.2 | -13.9 | S1S2 DZ | 84 | 16 | 4.2 | -9.9 | RR RC |
| 3019 | 184 | 44 | 9.9 | 1.4 | RR DZ | 100 | 18 | 5.8 | -1.0 | S1S2 DZ |
| 3020 | 206 | 56 | 9.7 | -4.5 | RR SV | 116 | 24 | 6.0 | -2.9 | RC DZ |
| 3021 | 156 | 38 | 6.1 | -0.5 | S1S2 DZ | 72 | 16 | 6.8 | 0.6 | RR RC |
| 3022 | 138 | 34 | 4.9 | -2.5 | RR DZ | 84 | 22 | 3.2 | -5.1 | RR RC |
| 3035 | 144 | 40 | 6.1 | -6.9 | RC DZ | 90 | 30 | 5.5 | 3.9 | S1S2 DZ |
| 3036 | 140 | 26 | 5.7 | -1.5 | RR RC | 90 | 22 | 5.3 | 1.2 | RR S1S2 |
| 3037 | 140 | 26 | 3.3 | -2.4 | S1S2 DZ | 92 | 16 | 1.9 | -0.4 | RR RC |
| 3038 | 150 | 34 | 7.7 | 7.7 | RC DZ | 96 | 26 | 5.0 | 1.4 | S1S2 DZ |
| 3039 | 152 | 18 | 3.6 | -1.0 | RR RC | 100 | 24 | 4.8 | -2.8 | RR RC |
| Average | | | 7.0 | 0.6 | | | | 6.2 | -0.4 | |

PATCH-BASED PHYSIOLOGICAL SENSOR

BACKGROUND AND FIELD OF THE INVENTION

1. Field of the Invention

The invention relates to the use of systems that measure physiological parameters from patients located, for example, in hospitals, clinics, and the home.

2. General Background

There are a number of physiological parameters that can be assessed by measuring biometric signals from a patient. Some signals, such as electrocardiogram (ECG), impedance plethysmogram (IPG), photoplethysmogram (PPG), and phonocardiogram (PCG) waveforms, are measured with sensors (e.g. electrodes, optics, microphones) that connect or attach directly to the patient's skin. Processing of these waveforms yields parameters such as heart rate (HR), heart rate variability (HRV), respiration rate (RR), pulse oximetry (SpO2), blood pressure (BP), stroke volume (SV), cardiac output (CO), and parameters related to thoracic impedance, for example thoracic fluid content (FLUIDS). Many physiological conditions can be identified from these parameters when they are obtained at a single point in time; others may require continuous assessment over long or short periods of time to identify trends in the parameters. In both cases, it is important to obtain the parameters with high repeatability and accuracy.

3. Known Devices and Relevant Physiology

Some devices that measure ECG waveforms are worn entirely on the patient's body. These devices often feature simple, patch-type systems that include both analog and digital electronics connected directly to underlying electrodes. Typically, these systems measure HR, HRV, RR, and, in some cases, posture, motion, and falls. Such devices are often prescribed for relatively short periods of time, such as a time period ranging from a few days to several weeks. They are typically wireless, and usually include technologies such as Bluetooth® transceivers to transmit information over a short range to a second device, which may include a cellular radio to transmit the information to a web-based system.

Bioimpedance medical devices measure SV, CO, and FLUIDS by sensing and processing time-dependent ECG and IPG waveforms. Typically, these devices connect to patients through disposable electrodes adhered at various locations on a patient's body. Disposable electrodes that measure ECG and IPG waveforms are typically worn on the patient's chest or legs and include: i) a conductive hydrogel that contacts the patient; ii) a Ag/AgCl-coated eyelet that contacts the hydrogel; iii) a conductive metal post that connects the eyelet to a lead wire or cable extending from the device; and iv) an adhesive backing that adheres the electrode to the patient. Medical devices that measure BP, including systolic (SYS), diastolic (DIA), and mean (MAP) BP, typically use cuff-based techniques called oscillometry or auscultation, or pressure-sensitive catheters than are inserted in a patient's arterial system. Medical devices that measure SpO2 are typically optical sensors that clip onto a patient's finger or earlobes, or attach through an adhesive component to the patient's forehead.

SUMMARY OF THE INVENTION

In view of the foregoing, it would be beneficial to improve the monitoring of patients in hospitals, clinics, and the home with a body-worn sensor. The sensor described herein is such a device: a neck-worn sensor resembling a conventional necklace or collar that non-invasively measures vital signs such as HR, HRV, RR, SpO2, TEMP, and BP, along with complex hemodynamic parameters such as SV, CO, and FLUIDS. The neck-worn sensor adheres to a patient's chest and continuously and non-invasively measures the above-mentioned parameters without cuffs and wires. In this way, it simplifies traditional protocols for taking such measurements, which typically involve multiple machines and can take several minutes to accomplish. The neck-worn sensor wirelessly transmits information to an external gateway (e.g. tablet, smartphone, or non-mobile, plug-in system) which can integrate with existing hospital infrastructure and notification systems, such as a hospital electronic medical records (EMR) system. With such a system, caregivers can be alerted to changes in vital signs, and in response can quickly intervene to help deteriorating patients. The neck-worn sensor can additionally monitor patients from locations outside the hospital.

More particularly, the invention features a neck-worn sensor that measures the following parameters from a patient: HR, PR, SpO2, RR, BP, TEMP, FLUIDS, SV, CO, and a set of parameters sensitive to blood pressure and systemic vascular resistance called pulse arrival time (PAT) and vascular transit time (VTT).

The neck-worn sensor also includes a motion-detecting accelerometer, from which it can determine motion-related parameters such as posture, degree of motion, activity level, respiratory-induced heaving of the chest, and falls. Such parameters could determine, for example, a patient's posture or movement during a hospital stay. The neck-worn sensor can operate additional algorithms to process the motion-related parameters to measure vital signs and hemodynamic parameters when motion is minimized and below a predetermined threshold, thereby reducing artifacts. Moreover, the neck-worn sensor estimates motion-related parameters such as posture to improve the accuracy of calculations for vital signs and hemodynamic parameters.

Disposable electrodes on a bottom surface of the neck-worn sensor secure it to the patient's body without requiring bothersome cables. The electrodes measure ECG and IPG waveforms. They easily connect (and disconnect) to circuit boards contained within the sensor by means of magnets. The magnets are electrically connected to the circuit boards to provide signal-conducting electrical couplings. Prior to use, the electrodes are simply held near the circuit boards, and magnetic attraction causes the electrode patches to snap into proper position, thereby ensuring proper positioning of the electrodes on the patient's body.

Using light-emitting diodes (LEDs) operating in the red (e.g. 660 nm) and infrared (e.g. 900 nm) spectral regions, the neck-worn sensor measures SpO2 by pressing lightly against capillary beds in the patient's chest. A heating element on the bottom surface of the neck-worn sensor contacts the patient's chest and gently warms the underlying skin, thereby increasing perfusion of the tissue. Operating with reflection-mode optics, the neck-worn sensor measures PPG waveforms with both red and infrared wavelengths. SpO2 is processed from alternating and static components of these waveforms, as is described in more detail below.

The neck-worn sensor measures all of the above-mentioned properties while featuring a comfortable, easy-towear form factor. It is lightweight (about 30 grams) and powered with a rechargeable battery. During use, it rests on the patient's chest, where the disposable electrodes hold it in place, as described in more detail below. The patient's chest is a location that is unobtrusive, comfortable, removed from the hands, and able to hold the sensor without being noticeable to the patient. It is also relatively free of motion compared to appendages such as the hands and fingers, and thus a sensor affixed to the chest region minimizes motion-related artifacts. Such artifacts are compensated for, to some degree, by the accelerometer within the sensor. Because the neck-worn sensor is a small and therefore considerably less noticeable or obtrusive than various other physiological sensor devices, emotional discomfort over wearing a medical device over an extended period of time is reduced, thereby fostering long-term patient compliance for use of this device within a monitoring regimen.

Given the above, in one aspect, the invention provides a neck-worn sensor for simultaneously measuring BP and SpO2 from a patient. The neck-worn sensor features a sensing portion having a flexible housing that is worn entirely on the patient's chest and encloses a battery, wireless transmitter, and all the sensor's sensing and electronic components. The sensor measures ECG, IPG, PPG, and PCG waveforms, and collectively processes these determine BP and SpO2. The sensor that measures PPG waveforms includes a heating element to increase perfusion of tissue on the chest.

On its bottom surface, the flexible housing includes an analog optical system, located proximal to one pair of the electrode contact points, that features a light source that generates radiation in both the red and infrared spectral ranges. This radiation separately irradiates a portion of the patient's chest disposed underneath the flexible housing. A photodetector detects the reflected radiation in the different spectral ranges to generate analog red-PPG and infrared-PPG waveforms.

A digital processing system disposed within the flexible housing includes a microprocessor and an analog-to-digital converter, and is configured to: 1) digitize the analog ECG waveform to generate a digital ECG waveform, 2) digitize the analog impedance waveform to generate a digital impedance waveform, 3) digitize the analog red-PPG waveform to generate a digital red-PPG waveform, 4) digitize the analog infrared-PPG waveform to generate a digital infrared-PPG waveform, and 5) digitize the analog PCG waveform to generate a digital PCG waveform. Once these waveforms are digitized, numerical algorithms operating in embedded computer code called 'firmware' process them to determine the parameters described herein.

In another aspect, the invention provides a neck-worn sensor for measuring a PPG waveform from a patient. The neck-worn sensor includes a housing worn on the patient's chest, and a heating element attached to the bottom surface of the housing so that, during use, it contacts and heats an area of the patient's chest. An optical system is located on a bottom surface of the housing and proximal to the heating element, and includes a light source that generates optical radiation that irradiates the area of the patient's chest during a measurement. The sensor also features a temperature sensor in direct contact with the heating element, and a closed-loop temperature controller within the housing and in electrical contact with the heating element and the temperature sensor. During a measurement, the closed-loop temperature controller receives a signal from the temperature sensor and, in response, controls an amount of heat generated by the heating element. A photodetector within the optical system generates the PPG waveform by detecting radiation that reflects off the area of the patient's chest after it is heated by the heating element.

Heating tissue that yields the PPG waveform typically increases blood flow (i.e. perfusion) to the tissue, thereby increasing the amplitude and signal-to-noise ratio of the waveform. This is particularly important for measurements made at the chest, where signals are typically significantly weaker than those measured from more conventional locations, such as the fingers, earlobes, and forehead.

In embodiments, the heating element features a resistive heater, such as a flexible film, metallic material, or polymeric material (e.g. Kapton®) that may include a set of embedded electrical traces that increase in temperature when electrical current passes through them. For example, the electrical traces may be disposed in a serpentine pattern to maximize and evenly distribute the amount of heat generated during a measurement. In other embodiments, the closed-loop temperature controller includes an electrical circuit that applies an adjustable potential difference to the resistive heater that is controlled by a microprocessor. Preferably, the microcontroller adjusts the potential difference it applies to the resistive heater so that its temperature is between 40-45° C.

In embodiments, the flexible-film heating element features an opening that transmits optical radiation generated by the light source so that it irradiates an area of the patient's chest disposed underneath the housing. In similar embodiments, the flexible film features a similar opening or set of openings that transmit optical radiation reflected from the area of the patient's chest so that it is received by the photodetector.

In still other embodiments, the housing further includes an ECG sensor that features a set of electrode leads, each configured to receive an electrode, that connect to the housing and electrically connect to the ECG sensor. For example, in embodiments, a first electrode lead is connected to one side of the housing, and a second electrode lead is connected to an opposing side of the housing. During a measurement, the ECG sensor receives ECG signals from both the first and second electrodes leads, and, in response, processes the ECG signals to determine an ECG waveform.

In another aspect, the invention provides a necklace-shaped sensor for measuring PPG and ECG waveforms from a patient that features an optical sensor, heating element, and temperature sensor similar to that described above. The sensor also includes a closed-loop temperature controller within the housing and in electrical contact with the heating element, the temperature sensor, and the processing system. The closed-loop temperature controller is configured to: 1) receive a first signal from the temperature sensor; 2) receive a second signal from the processing system corresponding to the second fiducial marker; 3) collectively process the first and second signals to generate a control parameter; and 4) control an amount of heat generated by the heating element based on the control parameter.

In embodiments, a software system included in the processing system determines a first fiducial marker within the ECG waveform that is one of a QRS amplitude, a Q-point, a R-point, an S-point, and a T-wave. Similarly, the software system determines a second fiducial marker that is one of an amplitude of a portion of the PPG waveform, a foot of a portion of the PPG waveform, and a maximum amplitude of a mathematical derivative of the PPG waveform.

In embodiments, the closed-loop temperature controller features an adjustable voltage source, and is configured to control an amount of heat generated by the heating element by adjusting the voltage source, e.g. the amplitude or frequency of a voltage generated by the voltage source.

In another aspect, the invention provides a similar necklace-shaped sensor that is worn on a patient's chest and measures PPG waveforms from the patient, and from these SpO2 values. The sensor features a similar heating element, temperature, closed-loop temperature controller, and optical system as described above. Here, the optical system generates optical radiation in both the red and infrared spectral regions. The sensor also includes an ECG sensor with at least two electrode leads and an ECG circuit that generates an ECG waveform. During a measurement, a processing system featuring a software system analyzes the ECG waveform to identify a first fiducial marker, and based on the first fiducial marker, identifies a first set of fiducial markers within the red PPG waveform, and a second set of fiducial markers within the infrared PPG waveform. The processing system then collectively processes the first and second set of fiducial markers to generate the SpO2 value.

In embodiments, for example, the first set of fiducials identified by the software system features an amplitude of a baseline of the red PPG waveform (RED(DC)) and an amplitude of a heartbeat-induced pulse within the red PPG waveform (RED(AC)), and the second set of fiducials identified by the software system features an amplitude of a baseline of the infrared PPG waveform (IR(DC)) and an amplitude of a heartbeat-induced pulse within the infrared PPG waveform (IR(AC)). The software system can be further configured to generate the SpO2 value from a ratio of ratios (R) by analyzing the RED(DC), RED(AC), IR(DC), and IR(AC) using the following equations, or mathematical equivalents thereof:

$$R = \frac{RED(AC)/RED(DC)}{IR(AC)/IR(DC)}$$

$$SpO2 = \frac{k_1 - k_2 \times R}{k_3 - k_4 \times R}$$

where $k_1$, $k_2$, $k_3$, and $k_4$ are pre-determined constants. Typically, these constants are determined during a clinical study called a 'breathe-down study' using a group of patients. During the study, the concentration of oxygen supplied to the patients is gradually lowered in sequential 'plateaus' so that their SpO2 values changes from normal values (near 98-100%) to hypoxic values (near 70%). As the concentration of oxygen is lowered, reference SpO2 values are typically measured at each plateau with a calibrated oximeter or a machine that measures oxygen content from aspirated blood. These are the 'true' SpO2 values. R values are also determined at each plateau from PPG waveforms measured by the neck-worn sensor. The pre-determined constants $k_1$, $k_2$, $k_3$, and $k_4$ can then be determined by fitting these data using equations shown above.

In other aspects, the invention provides a necklace-shaped sensor similar to that described above, that also includes an acoustic sensor for measuring PCG waveforms. Here, the sensor is mated with a single-use component that temporarily attaches to the sensor's housing and features a first electrode region positioned to connect to the first electrode contact point, a second electrode region positioned to connect to the second electrode contact point, and an impedance-matching region positioned to attach to the acoustic sensor.

In embodiments, the impedance-matching region comprises a gel or plastic material, and has an impedance at 100 kHz of about 220Ω. The acoustic sensor can be a single microphone or a pair of microphones. Typically, the sensor includes an ECG sensor that yields a signal that is then processed to determine a first fiducial point (e.g. a Q-point, R-point, S-point, or T-wave of a heartbeat-induced pulse in the ECG waveform). A processing system within the sensor processes the PCG waveform to determine the second fiducial point, which is either the S1 heart sound or S2 heart sound associated with a heartbeat-induced pulse in the PCG waveform. The processing system then determines a time difference separating the first fiducial point and the second fiducial point, and uses this time difference to determine the patient's blood pressure. Typically, a calibration measurement made by a cuff-based system is used along with the time difference to determine blood pressure.

In embodiments, the processor is further conjured to determine a frequency spectrum of the second fiducial point (using, e.g., a Fourier Transform), and then uses this to determine the patient's blood pressure.

In yet another aspect, the invention provides a chest-worn sensor similar to that described above. Here, the sensor features an optical system, located on a bottom surface of the sensor's housing, that includes: 1) a light source that generates optical radiation that irradiates an area of the patient's chest disposed underneath the housing; and 2) a circular array of photodetectors that surround the light source and detect optical radiation that reflects off the area of the patient's chest. As before, the area is heated with a heating element prior to a measurement.

In another aspect, the invention provides a neck-worn sensor for measuring a PPG waveform from a patient. The neck-worn sensor features a housing that is curved and flexible with unconnected first and second distal ends. During use, the housing drapes around the patient's neck so that the first distal end rests on the right-hand side of the patient's chest, and the second distal end rests on the left-hand side of the patient's chest. A heating element attaches to the bottom surface of either the first or second distal end of the housing so that it contacts and heats an area of the patient's chest when the housing is worn on the patient's chest. An optical system connected to the heating element features a light source that generates optical radiation that irradiates the area of the patient's chest. The sensor also includes a temperature sensor in direct contact with the heating element, and a closed-loop temperature controller within the housing and in electrical contact with both the heating element and the temperature sensor. During use, the closed-loop temperature controller receives a signal from the temperature sensor and, in response, controls an amount of heat generated by the heating element. A photodetector within the optical system generates a PPG waveform by detecting radiation that reflects off the area of the patient's chest after it is heated by the heating element.

In yet another aspect, the invention provides a neck-worn sensor for measuring PPG, PCG, and ECG waveforms from a patient. Here, the sensor features a housing composed of: 1) a first enclosure component featuring a first distal end; 2) a second enclosure component featuring a second distal end; and 3) a curved component connected on one side to the first enclosure component at a location opposite the first distal end, and on its opposing side to the second enclosure component at a location opposite to the second distal end. Collectively, the combined first enclosure component, second enclosure component, and curved component form a curved, contiguous housing that is approximately C-shaped and features a contiguous length (traced from one distal end to the other) between 590 and 630 mm. The resultant housing is configured so that the first and second distal ends remain unconnected and, during use, the curved component drapes around the patient's neck while the first distal end rests on the right-hand side of the patient's chest and the second distal end rests on the left-hand side of the patient's chest.

An optical sensor is disposed on the first distal end, and includes a light source for irradiating a portion of the patient's chest, and a photodetector for detecting radiation that reflects off the patient's chest to generate the PPG waveform. An acoustic sensor is disposed on the second distal end, and includes a sound-detecting sensor that detects heart sounds from the patient's chest to generate the PCG waveform.

The housing includes a first set of electrode leads disposed on the first distal end that connect to a first set of adhesive electrodes to secure the optical sensor to the patient's chest, and a second set of electrode leads disposed on the second distal end that connect to a second set of adhesive electrodes to secure the acoustic sensor to the patient's chest. An ECG sensor electrically connects to the first and second set of electrode leads, and is configured to receive bio-electric signals measured from the patient's chest by the first and second sets of adhesive electrodes and process them to determine the ECG waveform.

Advantages of the invention should be apparent from the following detailed description, and from the claims.

BRIEF DESCRIPTION OF THE DRAWINGS

FIG. 3A is a photograph of a back surface of the neck-worn sensor shown in FIG. 1, with the optical sensor emphasized;

FIG. 3B is a schematic swing of the optical sensor shown in FIG. 3A;

FIG. 5 is drawing a patient lying in a hospital bed and wearing the neck-worn sensor according to the invention, with the neck-worn sensor transmitting information through a gateway to a cloud-based system;

FIG. 6A is a time-dependent plot of an ECG waveform collected from a patient using a sensor similar to the neck-worn sensor of the invention, along with 'x' symbols marking fiducial points in the waveform;

FIG. 6B is a time-dependent plot of a PCG waveform collected simultaneously and from the same patient as the ECG waveform shown in FIG. 6A using a sensor similar to the neck-worn sensor of the invention, along with 'x' symbols marking fiducial points in the waveform;

FIG. 6C is a time-dependent plot of a PPG waveform collected simultaneously and from the same patient as the ECG waveform shown in FIG. 6A using a sensor similar to the neck-worn sensor of the invention, along with 'x' symbols marking fiducial points in the waveform;

FIG. 6D is a time-dependent plot of a IPG waveform collected simultaneously and from the same patient as the ECG waveform shown in FIG. 6A using a sensor similar to the neck-worn sensor of the invention, along with 'x' symbols marking fiducial points in the waveform;

FIG. 6E is a time-dependent plot of a mathematical derivative of the IPG waveform shown in FIG. 6D, along with 'x' symbols marking fiducial points in the waveform;

FIG. 7A is a time-dependent plot of ECG and PCG waveforms generated using a sensor similar to the neck-worn sensor from a single heartbeat from a patient, along with circular symbols marking fiducial points in these waveforms and indicating a time interval related to S2;

FIG. 7B is a time-dependent plot of an ECG waveform and the mathematical derivative of an IPG waveform generated using a sensor similar to the neck-worn sensor from a single heartbeat from a patient, along with circular symbols marking fiducial points in these waveforms and indicating a time interval related to B;

FIG. 7C is a time-dependent plot of an ECG waveform and the mathematical derivative of an IPG waveform generated using a sensor similar to the neck-worn sensor from a single heartbeat from a patient, along with an arrow symbol marking a amplitude related to $(dZ/dt)_{max}$;

FIG. 7D is a time-dependent plot of ECG and PPG waveforms generated using a sensor similar to the neck-worn sensor from a single heartbeat from a neck-worn patient, along with circular symbols marking fiducial points in these waveforms and indicating a time interval related to PAT;

FIG. 7E is a time-dependent plot of an ECG waveform and the mathematical derivative of an IPG waveform generated using a sensor similar to the neck-worn sensor from a single heartbeat from a patient, along with circular symbols marking fiducial points in these waveforms and indicating a time interval related to C;

FIG. 7F is a time-dependent plot of ECG and IPG waveforms generated using a sensor similar to the neck-worn sensor from a single heartbeat from a patient, along with an arrow symbol marking an amplitude related to $Z_o$;

FIG. 8A is a time-dependent plot of a PPG waveform measured with the optical sensor of FIG. 3B before heat is applied to an underlying surface of a patient's skin;

FIG. 8B is a time-dependent plot of a PPG waveform measured with the optical sensor of FIG. 3B after heat is applied to an underlying surface of a patient's skin;

FIG. 10 is a table showing results from a clinical trial conducted on 21 subjects that compared a cuffless BP measurement made by a sensor similar to the neck-worn sensor of FIG. 1 to a reference BP measurement performed using auscultation.

DETAILED DESCRIPTION

1. Neck-Worn Sensor

Figure 1:
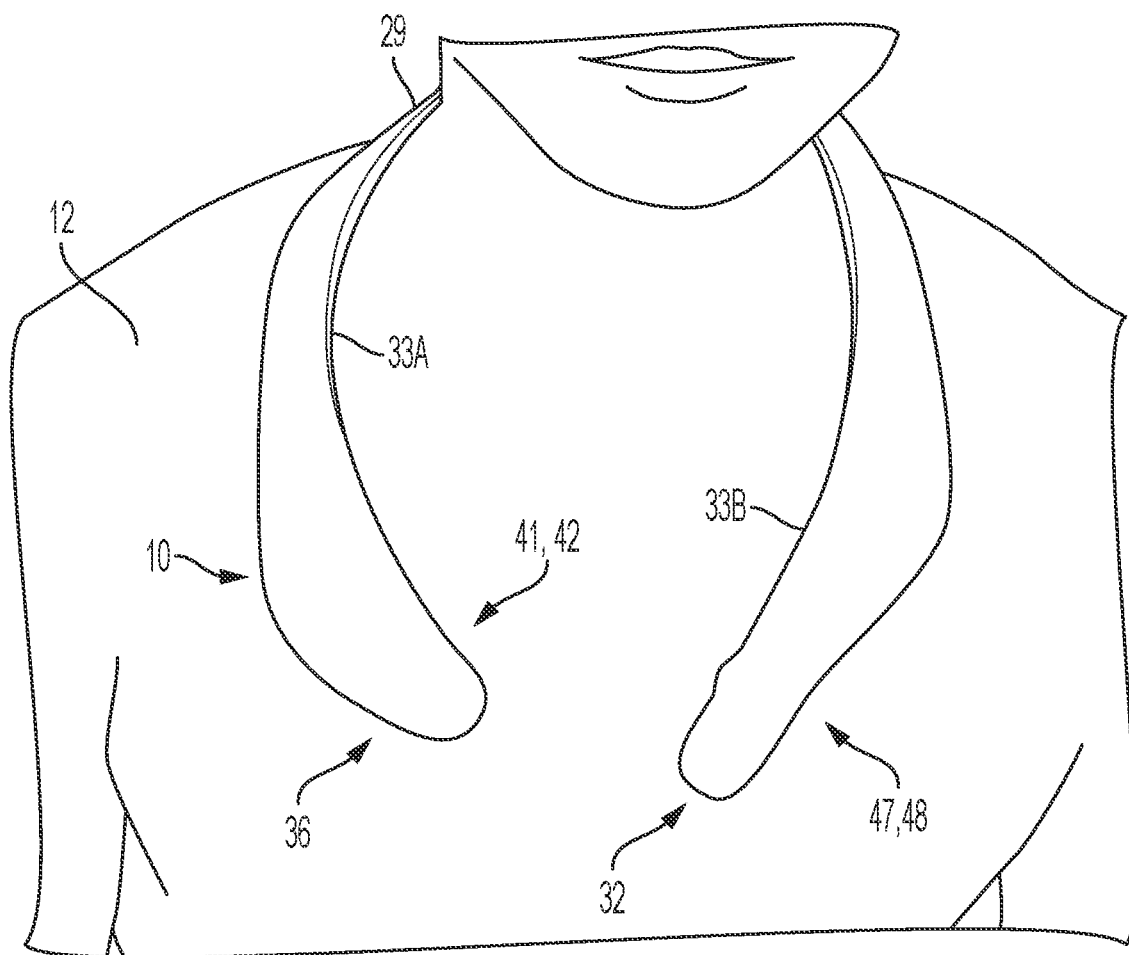
FIG. 1 is a schematic drawing showing a patient wearing a neck-worn sensor according to the invention.
Figure 2B:
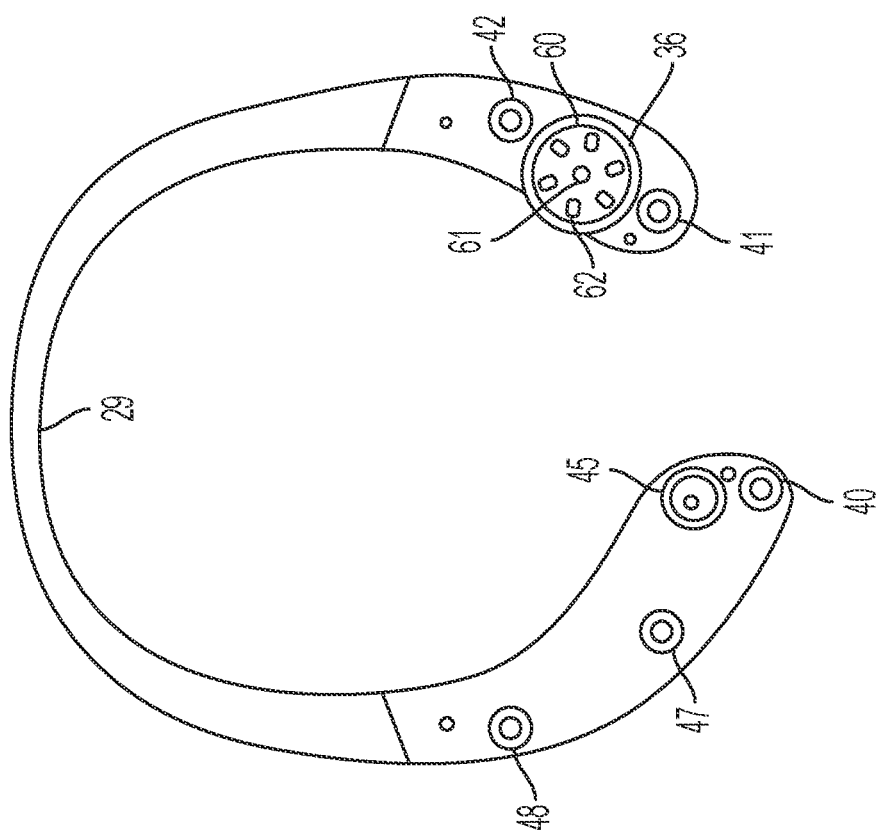
FIG. 2B is a photograph of a back surface of the neck-worn sensor shown in FIG. 1.
Figure 2A:
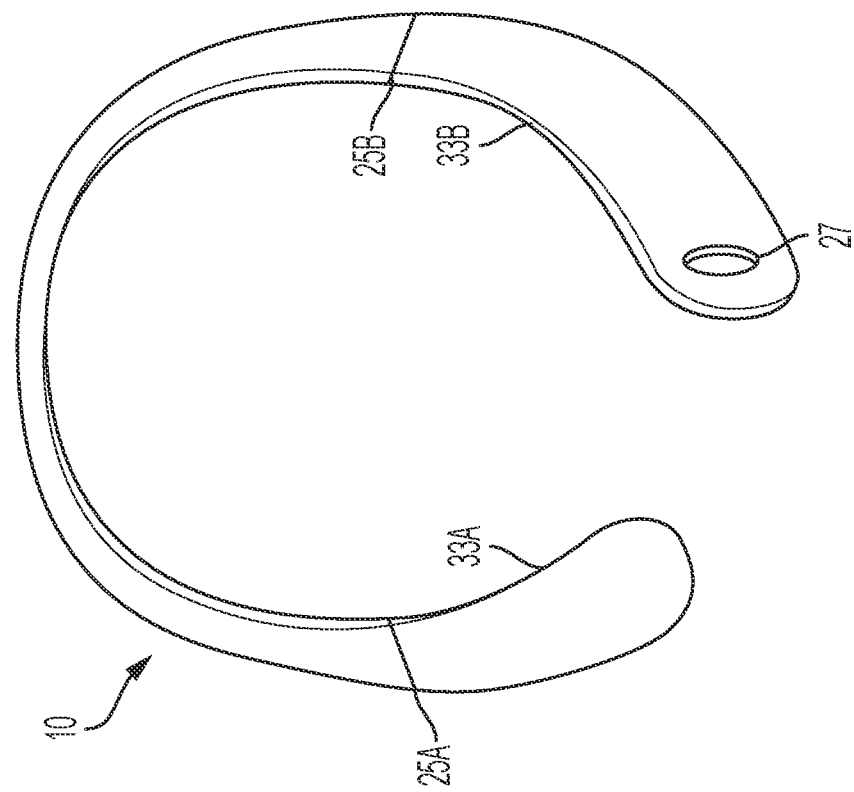
FIG. 2A is a photograph of a front surface of the neck-worn sensor shown in FIG. 1.

As shown in FIGS. 1, 2A, and 2B, a neck-worn sensor 10 according to the invention measures ECG, PPG, PCG, and IPG waveforms from a patient 12, and from these calculates vital signs (HR, HRV, SpO2, RR, BP, TEMP) and hemodynamic parameters (FLUIDS, SV, and CO) as described in detail below. Once this information is determined, the neck-worn sensor 10 wirelessly transmits it to an external gateway, which then forwards it to a cloud-based system. In this way, a clinician can continuously and non-invasively monitor the patient 12, who may be located in either the hospital or home.

The neck-worn sensor 10 drapes around the neck of a patient 12 like a necklace or collar. It features three primary components: 1) a first sensing portion 33A disposed on the right-hand side of the patient's chest; 2) a second sensing portion 33B disposed on the left-hand side of the patient's chest; and 3) a wire-carrying component 29 that wraps around the back portion of the patient's neck, and encloses conducting wires that electrically connect the first sensing portion 33A and the second sensing portion 33B. The first sensing portion 33A includes an optical sensor 36 that measures PPG waveforms from underlying capillary beds in the patient's chest. The optical sensor 36 is surrounded two electrode leads 41, 42 that connect to adhesive electrodes and help secure the neck-worn sensor 10 (and particularly the optical sensor 36) to the patient 12. The electrode leads 41, 42 also collect bio-electric signals from the patient, which are then used for ECG and IPG waveforms, as described in more detail below. The second sensing portion 33B includes an acoustic sensor 45 that measures sounds from the patient's heart that, after processing, yield PCG waveforms. Similar to the optical sensor 36, the acoustic sensor 45 is proximal to a pair of electrode leads 47, 48. Here, the electrode leads 47, 48 sit above the acoustic sensor 45 when the neck-worn sensor 10 is worn on the patient's chest, and are located on the opposite side of the chest from electrode leads 41, 42. They help secure the acoustic sensor 45 to the patient, and, like electrode leads 41, 42, collect bio-electric signals from the patient. A third electrode magnet 40 sits below the electrode leads 47, 48. The electrode magnet 40 connects to an adhesive component to help couple the acoustic sensor 45 to the chest, but, unlike electrode leads 47, 48, does not collect any bio-electric signal from the patient 12. Collectively, the three electrode leads 40, 47, 48 tightly secure the acoustic sensor 45 to the patient's chest during a measurement.

The first 33A and second 33B sensor portions are typically composed of a hard plastic material that protects circuitry components (not shown in the figure) disposed therein. The circuitry components are typically disposed on rigid fiberglass circuit boards, or alternatively a combination of rigid and flexible circuit boards, with one circuit board being housed in the first sensor portion 33A, and a second circuit board housed in the second sensor portion 33B. Electrical connections between the circuit boards are made with an electrical cable (also not shown in the figure) that solders to each of the circuit boards, and then snakes through the wire-carrying component 29. The first sensor portion 33A connects to one side of the wire-carrying component 29 through a first flexible joint 25A, and the second sensor portion 33B connects to an opposing side of the wire-carrying component 29 through a second flexible joint 25B. With this design, the neck-worn sensor 10 is inherently flexible and can conform to the inevitable curves in the patient's chest. In typical embodiments, to maximize comfort, the wire-carrying component 29 is composed of a hard plastic material that is overmolded with a soft rubber material. To accommodate patients of different sizes, the wire-carrying component 29 typically comes in different sizes (e.g. small, medium, and large), while the first 33A and second 33B sensor portions typically only come in one size. Such a design simplifies manufacturing and control over inventory associated with the neck-worn sensor 10.

Referring more specifically to FIG. 2B, the neck-worn sensor 10 includes a back surface that, during use, contacts the patient's chest through a set of single-use, adhesive electrodes (not shown in the figure). As described above, the first sensor portion 33A includes two electrode leads 41, 42, and the second sensor portion 33B includes two additional electrode leads 47, 48. Collectively, the electrode leads 41, 42, 47, 48 form two 'pairs' of leads, wherein one of the leads 41, 47 in each pair injects electrical current into the patient's chest to measure IPG waveforms, and the other leads 42, 48 in each pair sense bio-electrical signals that are then processed by electronics in the first 33A and second 33B sensor portions to determine both the ECG and IPG waveforms.

More specifically, the IPG measurement is made when the current-injecting electrodes 41, 47 inject high-frequency (e.g. 100 kHz), low-amperage (e.g. 4 mA) current into the patient's chest. The electrodes 42, 48 sense a voltage that indicates the impedance encountered by the injected current. The voltage passes through a series of electrical circuits featuring analog high and low-pass filters and differential amplifiers to, respectively, filter out and amplify signal components related to the two different waveforms. One of the signal components indicates the ECG waveform; another indicates the IPG waveform. The IPG waveform has low-frequency (DC) and high-frequency (AC) components that are further filtered out and processed, as described in more detail below, to determine different impedance waveforms.

The second sensor portion 33B includes a solid-state acoustic microphone 45 that measures heart sounds from the patient 12. The heart sounds are the 'lub, dub' sounds typically heard from the heart with a stethoscope; they indicate when the underlying mitral and tricuspid (S1, or 'lub' sound) and aortic and pulmonic (S2, or 'dub' sound) valves close (no detectable sounds are generated when the valves open). With signal processing, the heart sounds yield a PCG waveform that is used along with other signals to determine BP, as is described in more detail below. In embodiments, a second solid-state acoustic sensor (e.g. an additional microphone) can be added near the first acoustic sensor 45, and used to provide redundancy and better detect the sounds.

The optical sensor 36 features an optical system 60 that includes an array of photodetectors 62, arranged in a circular pattern, that surround a LED 61 that emits radiation in both the red and infrared spectral regions. During a measurement, sequentially emitted red and infrared radiation from the LED 61 irradiates and reflects off underlying tissue in the patient's chest, and is detected by the array of photodetectors 62. The detected radiation is modulated by blood flowing through capillary beds in the underlying tissue. Processing the reflected radiation with electronics results in PPG waveforms corresponding to the red and infrared radiation, which as described below are used to determine BP and SpO2.

The neck-worn sensor 10 also typically includes a three-axis digital accelerometer and a temperature sensor (not specifically identified in the figure) to measure, respectively, three time-dependent motion waveforms (along x, y, and z-axes) and TEMP values.

Figure 4:
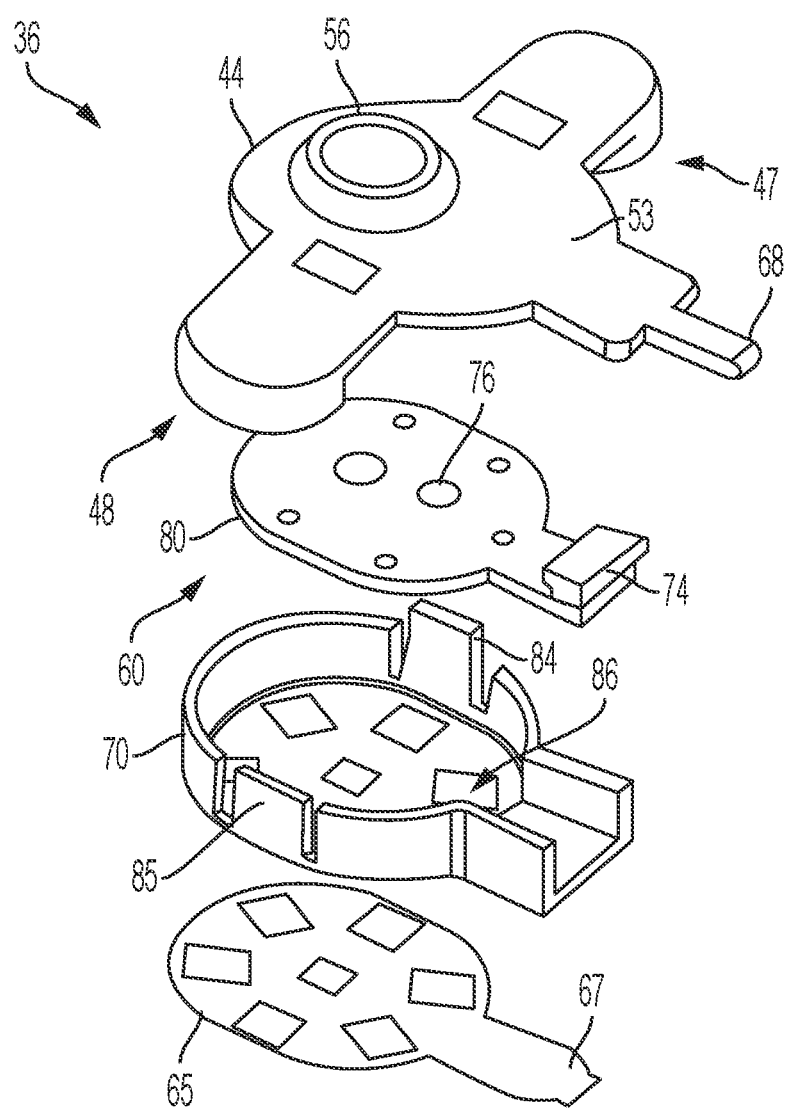
FIG. 4 is an exploded drawing of the optical sensor.

FIGS. 3A, 3B, and 4 show the optical sensor 36 in more detail. As described above, the sensor 36 features an optical system 60 with a circular array of photodetectors 62 (six unique detectors are shown in the figure, although this number can be between three and nine photodetectors) that surround a dual-wavelength LED 61 that emits red and infrared radiation. A heating element featuring a thin Kapton® film 65 with embedded electrical conductors arranged in a serpentine pattern is adhered to the bottom surface of the optical sensor 36. Other patterns of electrical conductors can also be used. The Kapton® film 65 features cut-out portions that pass radiation emitted by the LED 61 and detected by the photodetectors 62 after it reflects off the patient's skin. A tab portion 67 on the thin Kapton® film 65 folds over so it can plug into a connector 74 on a fiberglass circuit board 80. The fiberglass circuit board 80 supports and provides electrical connections to the array of photodetectors 62 and the LED 61. During use, software operating on the neck-worn sensor 10 controls power-management circuitry on the fiberglass circuit board 80 to apply a voltage to the embedded conductors within the thin Kapton® film 65, thereby passing electrical current through them. Resistance of the embedded conductors causes the film 65 to gradually heat up and warm the underlying tissue. The applied heat increases perfusion (i.e. blood flow) to the tissue, which in turn improves the signal-to-noise ratio of the PPG waveform. This is shown in FIG. 8A, which shows a PPG waveform measured before heat is applied, and FIG. 8B, which shows a PPG waveform measured after heat is applied with the Kapton® film 65. As is clear from the figures, heat increases the perfusion underneath the optical sensor 36. This, in turn, dramatically improves the signal-to-noise ratio of heartbeat-induced pulses in the PPG waveform. This is important for the neck-worn sensor's optical measurements, as PPG waveforms measured from the chest typically have a signal-to-noise ratio that is 10-100× weaker than similar waveforms measured from typical locations used by pulse oximeters, e.g. the fingers, earlobes, and forehead. PPG waveforms with improved signal-to-noise ratios typically improve the accuracy of BP and SpO2 measurements made by the neck-worn sensor 10. The fiberglass circuit board 80 also includes a temperature sensor 76 that integrates with the power-management circuitry, allowing the software to operate in a closed-loop manner to carefully control and adjust the applied temperature. Here, 'closed-loop manner' means that the software analyzes amplitudes of heartbeat-induced pulses the PPG waveforms, and, if necessary, increases the voltage applied to the Kapton® film 65 to increase its temperature and maximize the heartbeat-induced pulses in the PPG waveforms. Typically, the temperature is regulated at a level of between 41° C. and 42° C., which has been shown to not damage the underlying tissue, and is also considered safe by the U.S. Food and Drug Administration (FDA).

A plastic housing 44 featuring a top portion 53 and a bottom portion 70 enclose the fiberglass circuit board 80. The bottom portion 70 also supports the Kapton® film 65, has cut-out portions 86 that passes optical radiation, and includes a pair of snaps 84, 85 that connect to mated components on the top portion 53. The top portion also includes a pair of 'wings' that enclose the electrode leads 41, 42 which, during use, connect to the single-use, adhesive electrodes (not shown in the figure) that secure the optical sensor 36 to the patient. These electrode leads 41, 42 also measure electrical signals that are used for the ECG and IPG measurements, as described above.

The neck-worn sensor 10 typically measures waveforms at relatively high frequencies (e.g. 250 Hz). An internal microprocessor running firmware processes the waveforms with computational algorithms to generate vital signs and hemodynamic parameters with a frequency of about once every minute. Examples of algorithms are described in the following co-pending and issued patents, the contents of which are incorporated herein by reference: "NECK-WORN PHYSIOLOGICAL MONITOR," U.S. Ser. No. 14/975,646, filed Dec. 18, 2015; "NECKLACE-SHAPED PHYSIOLOGICAL MONITOR," U.S. Ser. No. 14/184,616, filed Aug. 21, 2014; and "BODY-WORN SENSOR FOR CHARACTERIZING PATIENTS WITH HEART FAILURE," U.S. Ser. No. 14/145,253, filed Jul. 3, 2014.

The neck-worn sensor 10 shown in FIGS. 1, 2A, 2B, 3A, 3B, and 4 is designed to maximize comfort and reduce 'cable clutter' when deployed on a patient, while at the same time optimizing the ECG, IPG, PPG, and PCG waveforms it measures to determine physiological parameters such as HR, HRV, BP, SpO2, RR, TEMP, FLUIDS, SV, and CO. The sensor 10 positions the first 33A and second 33B sensor portions so that the first pair of electrode leads 41, 42 are disposed on one side of the patient's heart, and the second pair of electrode leads 47, 48 are disposed on an opposite side of the patient's heart. In these locations, the bio-electrical signals are typically strong. As described above, this configuration results in ideal ECG and IPG waveforms, which are then used to calculate the physiological parameters described herein.

This neck-worn sensor's design also allows it to comfortably fit both male and female patients. An additional benefit of its chest-worn configuration is reduction of motion artifacts, which can distort waveforms and cause erroneous values of vital signs and hemodynamic parameters to be reported. This is due, in part, to the fact that during everyday activities, the chest typically moves less than the hands and fingers, and subsequent artifact reduction ultimately improves the accuracy of parameters measured from the patient.

2. Use Cases

As shown in FIG. 5, in a preferred embodiment, a neck-worn sensor 10 according to the invention is designed to monitor a patient 12 during a hospital stay. Typically, the patient 12 is situated in a hospital bed 11. As indicated above, in a typical use case, the neck-worn sensor 10 continuously measures numerical and waveform data, and then sends this information wirelessly (as indicated by arrow 77) to a gateway 22, which can be a number of different devices. For example, the gateway 22 can be any device operating a short-range wireless (e.g. Bluetooth®) wireless transmitter, e.g. a mobile telephone, tablet computer, vital sign monitor, central station (e.g. nursing station in a hospital), hospital bed, 'smart' television set, single-board computer, or a simple plug-in unit. The gateway 22 wirelessly forwards information (as indicated by arrow 87) from the neck-worn sensor 10 to a cloud-based software system 200. Typically, this is done with a wireless cellular radio, or one based on an 802.11a-g protocol. There, it can be consumed and processed by a variety of different software systems, such as a hospital EMR, a third-party software system, or a data-analytics engine.

In another embodiment, the sensor collects data and then stores it in internal memory. The data can then be sent wirelessly (e.g. to the cloud-based system, EMR, or central station) at a later time. For example, in this case, the gateway 22 can include an internal Bluetooth® transceiver that sequentially and automatically pairs with each sensor attached to a charging station. Once all the data collected during use are uploaded, the gateway then pairs with another sensor attached to the charging station and repeats the process. This continues until data from each sensor is downloaded.

In other embodiments, the neck-worn sensor can be used to measure ambulatory patients, patients undergoing dialysis in either the hospital, clinic, or at home, or patients waiting to see a doctor in a medical clinic. Here, the neck-worn sensor can transmit information in real time, or store it in memory for transmission at a later time.

3. Determining Cuffless Blood Pressure

The neck-worn sensor determines BP by collectively processing time-dependent ECG, IPG, PPG, and PCG waveforms, as shown in FIGS. 6A-E. Each waveform is typically characterized by a heartbeat-induced 'pulse' that is affected in some way by BP. More specifically, embedded firmware operating on the neck-worn sensor processes pulses in these waveforms with 'beatpicking' algorithms to determine fiducial makers corresponding to features of each pulse; these markers are then processed with algorithms, described below, to determine BP. In FIGS. 6A-E, the fiducial makers for pulses within the ECG, IPG, PPG, and PCG waveforms are indicated with 'x' symbols.

An ECG waveform measured by the neck-worn sensor is shown in FIG. 6A. It includes a heartbeat-induced QRS complex that informally marks the beginning of each cardiac cycle. FIG. 6B shows a PCG waveform, which is measured with the acoustic module and features the S1 and S2 heart sounds. FIG. 6C shows a PPG waveform, which is measured by the optical sensor, and indicates volumetric changes in underlying capillaries caused by heartbeat-induced blood flow. The IPG waveform includes both DC ($Z_0$) and AC (dZ(t)) components: $Z_0$ indicates the amount of fluid in the chest by measuring underlying electrical impedance, and represents the baseline of the IPG waveform; dZ(t), which is shown in FIG. 6D, tracks blood flow in the thoracic vasculature and represents the pulsatile components of the IPG waveform. The time-dependent derivative of dZ(t) –dZ(t)/dt– includes a well-defined peak that indicates the maximum rate of blood flow in the thoracic vasculature, and is shown in FIG. 6E.

Each pulse in the ECG waveform (FIG. 6A) features a QRS complex that delineates a single heartbeat. Feature-detection algorithms operating in firmware on the neck-worn sensor calculate time intervals between the QRS complex and fiducial markers on each of the other waveforms. For example, the time separating a 'foot' of a pulse in the PPG waveform (FIG. 6C) and the QRS complex is referred to as PAT. PAT relates to BP and systemic vascular resistance. During a measurement, the neck-worn sensor calculates PAT and VTT which is a time difference between fiducial markers in waveforms other than ECG, e.g. the S1 or S2 points in a pulse in the PCG waveform (FIG. 6B) and the foot of the PPG waveform (FIG. 6C). Or the peak of a pulse in the dZ(t)/dt waveform (FIG. 6E) and the foot of the PPG waveform (FIG. 6C). In general, any set of time-dependent fiducials determined from waveforms other than ECG can be used to determine VTT. Collectively, PAT, VTT, and other time-dependent parameters extracted from pulses in the four physiologic waveforms are referred to herein as 'INT' values. Additionally, firmware in the neck-worn sensor calculates information about the amplitudes of heartbeat-induced pulses in some of the waveforms; these are referred to herein as 'AMP' values. For example, the amplitude of the pulse in the derivative of the AC component of the IPG waveform ((dZ(t)/dt)max as shown in FIG. 6E) indicates the volumetric expansion and forward blood flow of the thoracic arteries, and is related to SYS and the contractility of the heart.

The general model for calculating SYS and DIA involves extracting a collection of INT and AMP values from the four physiologic waveforms measured by the neck-worn sensor. FIGS. 7A-F, for example, show different INT and AMP values that may correlate to BP. INT values include the time separating R and S2 from a pulse in the PCG waveform (RS2, shown in FIG. 7A); the time separating R and the base of a derivative of a pulse from the AC component of the IPG waveform (RB, FIG. 7B); the time separating R and the foot of a pulse in the PPG waveform (PAT, FIG. 7D); and the time separating R and the maximum of a derivative of a pulse from the AC component of the IPG waveform (RC, FIG. 7E). AMP values include the maximum value of a derivative of a pulse from the AC component of the IPG waveform ((dZ(t)/dt)max, FIG. 7C); and the maximum value of the DC component of the IPG waveform ($Z_0$, FIG. 7F). Any of these parameters may be used, in combination with a calibration defined below, to determine blood pressure.

The method for determining BP according to the invention involves first calibrating the BP measurement during a short initial period, and then using the resulting calibration for subsequent measurements. The calibration process typically lasts for about 5 days. It involves measuring the patient multiple (e.g. 2-4) times with a cuff-based BP monitor employing oscillometry, while simultaneously collecting the INT and AMP values like those shown in FIGS. 7A-F. Each cuff-based measurement results in separate values of SYS, DIA, and MAP. In embodiments, one of the cuff-based BP measurements may be coincident with a 'challenge event' that alters the patient's BP, e.g. squeezing a handgrip, changing posture, or raising their legs. The challenge events typically impart variation in the calibration measurements; this can help improve the ability of the calibration to track BP swings. Typically, the neck-worn sensor and cuff-based BP monitor are in wireless communication with each other; this allows the calibration process to be fully automated, e.g. information between the two systems can be automatically shared without any user input. Processing the INT and AMP values, e.g. using the method shown in FIG. 9 and described in more detail below, results in a 'BP calibration'. This includes initial values of SYS and DIA, which are typically averaged from the multiple measurements made with the cuff-based BP monitor, along with a patient-specific model that is used in combination with selected INT and AMP values to cufflessly determine the patient's blood pressure. The calibration period (about 5 days), is consistent with a conventional hospital stay; after this, the neck-worn sensor typically requires a new calibration to ensure accurate BP measurements.

Figure 9:
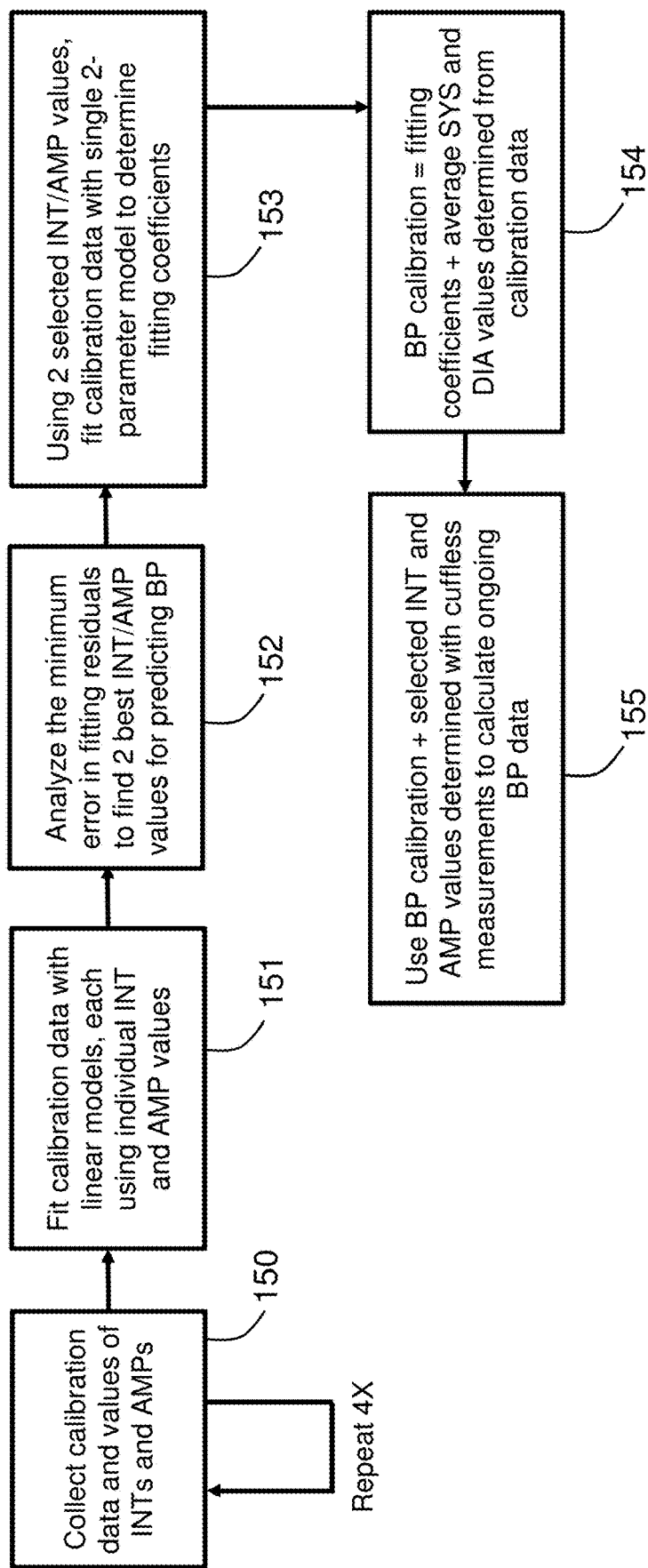
FIG. 9 is a flow chart showing an algorithm used by the neck-worn sensor to measure cuffless BP.

FIG. 9 is a flowchart that indicates how the BP calibration is determined, and how cuffless BP values are then calculated using the BP calibration. The process starts by collecting calibration data (step 150) that includes values of SYS and DIA. These data are collected along with INT and AMP values for each measurement. Typically, this process is repeated four times, with one instance coinciding with a challenge event, as described above. Using embedded firmware operating on the neck-worn sensor, the calibration data is then 'fit' with multiple linear models (step 151) to determine which individual INT and AMP values best predict the patient's SYS and DIA values, as measured with the cuff-based BP monitor. Here, the term 'fit' means using an iterative algorithm, such as a Levenberg-Marquardt (LM) fitting algorithm, to process the INT/AMP values to estimate the calibration data. The LM algorithm is also known as the damped least-squares (DLS) method, and is used to solve non-linear least squares problems. These minimization problems arise especially in least squares curve fitting. The INT and AMP values selected using the LM algorithm are those that yield the minimum error between the fits and calibration data (step 152); here, the error can be the 'residual' of the fit, or alternatively a root-mean squared error (RMSE) between the fit and the calculated data. Typically, two ideal INT/AMP values are selected with this process. Once selected, the two ideal INT/AMP values are then combined into a single, two-parameter linear model, which is then used to fit calibration data once again (step 153). The fitting coefficients that are determined from this fitting process, along with the average, initial values of SYS and DIA determined from the calibration data, represent the BP calibration (step 154). This process is done independently for SYS and DIA, meaning that one set of INT/AMP values may be used for the BP calibration for SYS, and another set used for the BP calibration for DIA.

Once determined, the BP calibration is then used to calculate cuffless BP values going forward. Specifically, for a post-calibration cuffless measurement, the selected INT/AMP values (2 total) are measured from the time-dependent ECG, IPG, PPG, and PCG waveforms. These values are then combined in a linear model with the BP calibration (fitting coefficients and average, initial values of SYS and DIA), which is then used to calculate BP (step 155).

4. Clinical Results

The table 170 shown in FIG. 10 indicates the efficacy of this approach for both SYS and DIA. Data in the table were collected using a clinical study performed over a 3-day period with 21 subjects. In total, the clinical study was conducted over a 2-week period, starting in December 2017 at a single study site in the greater San Diego area. All measurements were made while the subjects rested in a supine position in a hospital bed. A BP calibration was determined on the first day of the study (Day 1) for each subject using the approach described above and shown in FIG. 9. Once the BP calibration was determined, the subject was dismissed, and then returned 2 days later (Day 3) for a cuffless BP measurement. The BP calibration on Day 1 was used along with the selected INT/AMP values to determine cuffless BP values on Day 3, where 10 measurements were made periodically over a period of about 2 hours, all while the subject was resting in a supine position. For most subjects, at least one of the 10 measurements featured a challenge event, as described above, which typically elevated the subject's BP. And for each of the 10 measurements, cuffless BP values were compared to reference BP values measured with a 'gold-standard technique', which in this case was a clinician measuring blood pressure using a technique called auscultation, which is performed using a cuff-based sphygmomanometer.

The table 170 includes the following columns:

Column 1—subject number

Column 2—maximum reference value of SYS (units mmHg)

Column 3—range in reference values of SYS (units mmHg)

Column 4—standard deviation calculated from the difference between the reference and cuffless values of SYS measured on Day 3 (10 measurements total, units mmHg)

Column 5—bias calculated from the difference between the reference and cuffless values of SYS measured on Day 3 (10 measurements total, units mmHg)

Column 6—selected INT/AMP values used in the cuffless measurement of SYS

Column 7—maximum reference value of DIA (units mmHg)

Column 8—range in reference values of DIA (units mmHg)

Column 9—standard deviation calculated from the difference between the reference and cuffless values of DIA measured on Day 3 (10 measurements total, units mmHg)

Column 10—bias calculated from the difference between the reference and cuffless values of DIA measured on Day 3 (10 measurements total, units mmHg)

Column 11—selected INT/AMP values used in the cuffless measurement of DIA

As shown in the table 170, the average standard deviation and bias calculated from the difference between the reference and cuffless values of SYS measured on Day 3 were 7.0 and 0.6 mmHg, respectively. The corresponding values for DIA were 6.2 and −0.4 mmHg, respectively. These values are within those recommended by the U.S. FDA (standard deviation less than 8 mmHg, bias less than ±5 mmHg), and thus indicate that the cuffless BP measurement of the invention has suitable accuracy.

5. Alternative Embodiments

Figure 11:
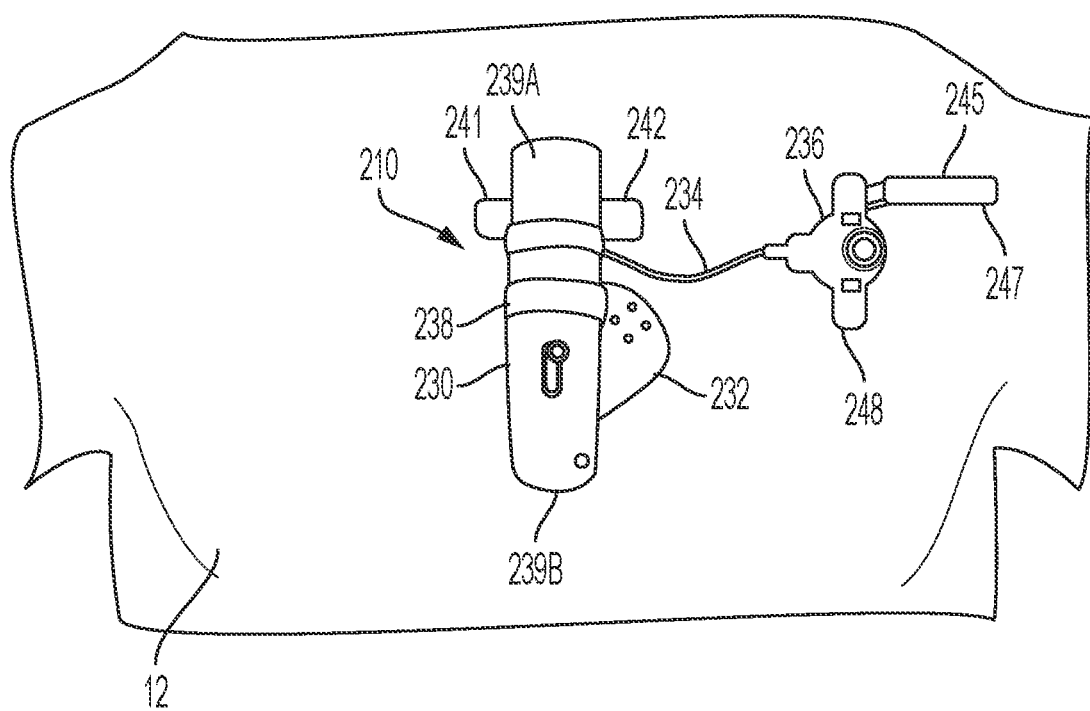
FIG. 11 is a schematic drawing showing a patient wearing an alternate embodiment of the neck-worn sensor according to the invention.

The neck-worn sensor described herein can have a form factor that differs from that shown in FIG. 1. FIG. 11, for example, shows such an alternate embodiment. Similar to the preferred embodiment described above, a patch sensor 210 in FIG. 11 features two primary components: a central sensing/electronics module 230 worn near the center of the patient's chest, and an optical sensor 236 worn near the patient's left shoulder. Electrode leads 241, 242 measure bio-electrical signals for the ECG and IPG waveforms and secure the central sensing/electronics module 230 to the patient 12, similar to the manner as described above. A flexible, wire-containing cable 234 connects the central sensing/electronics module 230 and the optical sensor 236. In this case, the central sensing/electronics module 230 features a substantially rectangular shape, as opposed to a substantially circular shape shown in FIG. 1. The optical sensor 236 includes two electrode leads 247, 248 that connect to adhesive electrodes and help secure the patch sensor 210 (and particularly the optical sensor 236) to the patient 12. The distal electrode lead 248 connects to the optical sensor through an articulating arm 245 that allows it to extend further out near the patient's shoulder, thereby increasing its separation from the central sensing/electronics module 230.

The central sensing/electronics module 230 features two halves 239A, 239B, each housing sensing and electronic components that are separated by a flexible rubber gasket 238. The central sensing/electronics module 230 connects an acoustic module 232, which is positioned directly above the patient's heart. Flexible circuits (not shown in the figure) typically made of a Kapton® with embedded electrical traces) connect fiberglass circuit boards (also not shown in the figure) within the two halves 239A, 239B of the central sensing/electronics module 230.

The electrode leads 241, 242, 247, 248 form two 'pairs' of leads, wherein one of the leads 241, 247 injects electrical current to measure IPG waveforms, and the other leads 242, 248 sense bio-electrical signals that are then processed by electronics in the central sensing/electronics module 230 to determine the ECG and IPG waveforms.

The acoustic module 232 includes one or more solid-state acoustic microphones (not shown in the figure, but similar to that shown in FIG. 1) that measure heart sounds from the patient 12. The optical sensor 236 attaches to the central sensing/electronics module 30 through the flexible cable 234, and features an optical system (also not shown in the figure, but similar to that shown in FIG. 1) that includes an array of photodetectors, arranged in a circular pattern, that surround a LED that emits radiation in the red and infrared spectral regions. During a measurement, sequentially emitted red and infrared radiation emitted from the LED irradiates and reflects off underlying tissue in the patient's chest, and is detected by the array of photodetectors.

In other embodiments, an amplitude of either the first or second (or both) heart sound is used to predict blood pressure. Blood pressure typically increases in a linear manner with the amplitude of the heart sound. In embodiments, a universal calibration describing this linear relationship may be used to convert the heart sound amplitude into a value of blood pressure. Such a calibration, for example, may be determined from data collected in a clinical trial conducted with a large number of subjects. Here, numerical coefficients describing the relationship between blood pressure and heart sound amplitude are determined by fitting data determined during the trial. These coefficients and a linear algorithm are coded into the sensor for use during an actual measurement. Alternatively, a patient-specific calibration can be determined by measuring reference blood pressure values and corresponding heart sound amplitudes during a calibration measurement, which proceeds an actual measurement. Data from the calibration measurement can then be fit as described above to determine the patient-specific calibration, which is then used going forward to convert heart sounds into blood pressure values.

Both the first and second heart sounds are typically composed of a collection, or 'packet' of acoustic frequencies. Thus, when measured in the time domain, the heart sounds typically feature a number of closely packed oscillations within to the packet. This can make it complicated to measure the amplitude of the heart sound, as no well-defined peak is present. To better characterize the amplitude, a signal-processing technique can be used to draw an envelope around the heart sound, and then measure the amplitude of the envelope. One well-known technique for doing this involves using a Shannon Energy Envelogram (E(t)), where each data point within E(t) is calculated as shown below:

$$E_{average} = -\frac{1}{N}\sum_{t=1}^{N}[PCG^2(t) \times \log(PCG^2(t))]$$

where N is the window size of E(t). In embodiments, other techniques for determining the envelope of the heart sound can also be used.

Once the envelope is calculated, its amplitude can be determined using standard techniques, such as taking a time-dependent derivative and evaluating a zero-point crossing. Typically, before using it to calculate blood pressure, the amplitude is converted into a normalized amplitude by dividing it by an initial amplitude value measured from an earlier heart sound (e.g., one measured during calibration). A normalized amplitude means the relative changes in amplitude are used to calculate blood pressure; this typically leads to a more accurate measurement.

In other embodiments, an external device may be used to determine how well the acoustic sensor is coupled to the patient. Such an external device, for example, may be a piezoelectric 'buzzer', or something similar, that generates an acoustic sound and is incorporated into the neck-worn sensor, proximal to the acoustic sensor. Before a measurement, the buzzer generates an acoustic sound at a known amplitude and frequency. The acoustic sensor measures the sound, and then compares its amplitude (or frequency) to other historical measurements to determine how well the acoustic sensor is coupled to the patient. An amplitude that is relatively low, for example, indicates that the sensor is poorly coupled. This scenario may result in an alarm alerting the user that the sensor should be reapplied.

In still other alternative embodiments, the invention may use variation of algorithms for finding INT and AMP values, and then processing these to determine BP and other physiological parameters. For example, to improve the signal-to-noise ratio of pulses within the IPG, PCG, and PPG waveforms, embedded firmware operating on the neck-worn sensor can operate a signal-processing technique called 'beatstacking'. With beatstacking, for example, an average pulse (e.g. Z(t)) is calculated from multiple (e.g. seven) consecutive pulses from the IPG waveform, which are delineated by an analysis of the corresponding QRS complexes in the ECG waveform, and then averaged together. The derivative of Z(t) −dZ(t)/dt− is then calculated over an 7-sample window. The maximum value of Z(t) is calculated, and used as a boundary point for the location of $[dZ(t)/dt]_{max}$. This parameter is used as described above. In general, beatstacking can be used to determine the signal-to-noise ratio of any of the INT/AMP values described above.

In other embodiments, the BP calibration process indicated by the flow chart in FIG. 9 can be modified. For example, it may select more than two INT/AMP values to use for the multi-parameter linear fitting process. And the BP calibration data may be calculated with less than or more than four cuff-based BP measurements. In still other embodiments, a non-linear model (e.g. one using a polynomial or exponential function) may be used to fit the calibration data.

In still other embodiments, a sensitive accelerometer can be used in place of the acoustic sensor to measure small-scale, seismic motions of the chest driven by the patient's underlying beating heart. Such waveforms are referred to as seismocardiogram (SCG) and can be used in place of (or in concert with) PCG waveforms.

These and other embodiments of the invention are deemed to be within the scope of the following claims.

What is claimed is:

1. A sensor for measuring a photoplethysmogram (PPG) waveform from a patient, the sensor comprising:
a primary housing, wherein during use the primary housing is configured to rest entirely on a middle of the patient's chest, the primary housing comprising a first portion and a second portion, the first portion disposed above the second portion;
a secondary housing, coupled to the primary housing via a flexible wire, the secondary housing including a heating element, a temperature sensor, and an optical system, wherein the secondary housing is disposed adjacent to a shoulder, and wherein:
 the heating element is attached to the bottom surface of the secondary housing so that the heating element contacts and heats an area adjacent to the shoulder;
 the optical system connected to the heating element, the optical system comprising a light source configured to generate optical radiation that irradiates the area adjacent to the shoulder and a photodetector comprised by the optical system and configured to generate a PPG waveform by detecting radiation that reflects off the area adjacent to the shoulder after it is heated by the heating element;

the temperature sensor is in direct contact with the heating element; and a closed-loop temperature controller comprised within the secondary housing and in electrical contact with each of the heating element and the temperature sensor, the closed-loop temperature controller configured to receive a first signal from the temperature sensor and a second signal related to the PPG waveform and, in response, control an amount of heat generated by the heating element.

2. The sensor of claim 1, wherein the heating element comprises a resistive heater.

3. The sensor of claim 2, wherein the resistive heater is a flexible film.

4. The sensor of claim 3, wherein the resistive heater comprises a set of electrical traces configured to increase in temperature when electrical current passes through them.

5. The sensor of claim 3, wherein the flexible film is a polymeric material.

6. The sensor of claim 5, wherein the polymeric material comprises Kapton®.

7. The sensor of claim 3, wherein the flexible film comprises an opening that transmits optical radiation generated by the light source so that it irradiates an area adjacent to the shoulder disposed underneath the secondary housing.

8. The sensor of claim 3, wherein the flexible film comprises an opening that transmits optical radiation reflected from the area adjacent to the shoulder so that it is received by the photodetector.

9. The sensor of claim 2, wherein the closed-loop temperature controller comprises an electrical circuit that applies a potential difference to the resistive heater.

10. The sensor of claim 9, wherein the closed-loop temperature controller comprises a microprocessor configured to process the first signal from the temperature sensor, and, in response, adjust the potential difference it applies to the resistive heater.

11. The sensor of claim 10, wherein the microprocessor comprises computer code configured to process the first signal from the temperature sensor, and, in response, adjust the potential difference it applies to the resistive heater so that its temperature is between 40-45° C.

12. The sensor of claim 1, wherein the primary housing further comprises an electrocardiogram (ECG) sensor.

13. The sensor of claim 12, where a set of electrode leads, each configured to receive an electrode, connect to the primary housing and electrically connect to the ECG sensor.

14. The sensor of claim 13, wherein a first electrode lead is connected to one side of the primary housing, and a second electrode lead is connected to an opposing side of the primary housing.

15. The sensor of claim 12, wherein the ECG sensor receives an ECG signal from at least one of a first and second electrodes leads, and, in response, processes the ECG signal to determine an ECG waveform.

16. A sensor for measuring a photoplethysmogram (PPG) waveform from a patient, the sensor comprising:

a primary housing, wherein during use the primary housing is configured to rest entirely on a middle of the patient's chest, the primary housing comprising a first portion and a second portion, the first portion disposed above the second portion;

a secondary housing, coupled to the primary housing via a flexible wire, the secondary housing including a heating element, a temperature sensor, and an optical system, wherein the secondary housing is disposed adjacent to a shoulder, and wherein:

the heating element is attached to a bottom surface of the secondary housing so that the heating element contacts and heats an area adjacent to the shoulder;

the temperature sensor is in direct contact with the heating element;

the optical system located proximal to the heating element, the optical system comprising a light source configured to generate optical radiation that irradiates the area adjacent to the shoulder, and a photodetector configured to generate a PPG waveform by detecting radiation that reflects off the area adjacent to the shoulder after it is heated by the heating element; and a closed-loop temperature controller comprised within the secondary housing and in electrical contact with each of the heating element and the temperature sensor, the closed-loop temperature controller configured to receive a first signal from the temperature sensor and a second signal related to the PPG waveform and, in response, control an amount of heat generated by the heating element.

17. The sensor of claim 16, wherein the heating element comprises a resistive heater.

18. The sensor of claim 17, wherein the resistive heater is a flexible film.

19. The sensor of claim 18, wherein the resistive heater comprises a set of electrical traces configured to increase in temperature when electrical current passes through them.

20. The sensor of claim 18, wherein the flexible film is a polymeric material.

21. The sensor of claim 20, wherein the polymeric material comprises Kapton®.

22. The sensor of claim 18, wherein the flexible film comprises a first opening that transmits optical radiation generated by the light source so that it irradiates the area adjacent to the shoulder disposed underneath the secondary housing.

23. The sensor of claim 18, wherein the flexible film comprises a second opening that transmits optical radiation reflected from the area adjacent to the shoulder so that it is received by the photodetector.

24. The sensor of claim 17, wherein the closed-loop temperature controller comprises an electrical circuit that applies a potential difference to the resistive heater.

25. The sensor of claim 24, wherein the closed-loop temperature controller comprises a microprocessor configured to process the first signal from the temperature sensor, and, in response, adjust the potential difference it applies to the resistive heater.

26. The sensor of claim 25, wherein the microprocessor comprises computer code configured to process the second signal from the temperature sensor, and, in response, adjust the potential difference it applies to the resistive heater so that its temperature is between 40-45° C.

27. The sensor of claim 16, wherein the primary housing further comprises an electrocardiogram (ECG) sensor.

28. The sensor of claim 27, where a set of electrode leads, each configured to receive an electrode, connect to the primary housing and electrically connect to the ECG sensor.

29. The sensor of claim 28, wherein a first electrode lead is connected to one side of the primary housing, and a second electrode lead is connected to an opposing side of the primary housing.

30. The sensor of claim 28, wherein the ECG sensor receives an ECG signal from at least one of a first and second electrodes leads, and, in response, processes the ECG signal to determine an ECG waveform.

* * * * *